United States Patent
Kohara et al.

(10) Patent No.: US 9,804,094 B2
(45) Date of Patent: Oct. 31, 2017

(54) PLASMA SPECTROMETER

(71) Applicant: HITACHI HIGH-TECHNOLOGIES CORPORATION, Tokyo (JP)

(72) Inventors: Yoshinobu Kohara, Tokyo (JP); Yuzuru Takamura, Ishikawa (JP)

(73) Assignee: Hitachi High-Technologies Corporation, Tokyo (JP)

( * ) Notice: Subject to any disclaimer, the term of this patent is extended or adjusted under 35 U.S.C. 154(b) by 34 days.

(21) Appl. No.: 14/383,119

(22) PCT Filed: Nov. 20, 2012

(86) PCT No.: PCT/JP2012/080524
§ 371 (c)(1),
(2) Date: Sep. 5, 2014

(87) PCT Pub. No.: WO2013/132706
PCT Pub. Date: Sep. 12, 2013

(65) Prior Publication Data
US 2015/0015880 A1  Jan. 15, 2015

(30) Foreign Application Priority Data
Mar. 7, 2012 (JP) ................. 2012-050497

(51) Int. Cl.
*G01J 3/30* (2006.01)
*G01N 21/67* (2006.01)
*G01N 21/05* (2006.01)

(52) U.S. Cl.
CPC ............. *G01N 21/67* (2013.01); *G01N 21/05* (2013.01); *G01N 2201/067* (2013.01); *G01N 2201/08* (2013.01)

(58) Field of Classification Search
CPC ........ G01N 21/67; G01N 21/68; G01N 21/69; G01N 21/05
See application file for complete search history.

(56) References Cited

U.S. PATENT DOCUMENTS

| | | | | |
|---|---|---|---|---|
| 3,144,551 A | * | 8/1964 | Webb | ..................... G01N 21/67 356/307 |
| 5,407,638 A | * | 4/1995 | Wang | ..................... G01N 21/05 250/576 |
| 5,690,895 A | * | 11/1997 | Matsumoto | ........ G01N 15/1404 356/246 |

(Continued)

FOREIGN PATENT DOCUMENTS

| | | |
|---|---|---|
| JP | 04-366749 A | 12/1992 |
| JP | 10-300671 A | 11/1998 |
| JP | 3932368 B2 | 3/2007 |

(Continued)

*Primary Examiner* — Michael A Lyons
(74) *Attorney, Agent, or Firm* — Mattingly & Malur, PC

(57) ABSTRACT

To improve the detection sensitivity, detection accuracy, and reproducibility when electrostatic discharge is generated in a sample solution and analysis is performed using light emission in the generated plasma. A flow channel 100, which has cylindrical main portions each expanding conically from a narrow portion, is filled with a conductive sample solution, and an electric field is applied to the flow channel 100 to generate plasma in the generated air bubbles, so that the resulting light emission is measured.

13 Claims, 12 Drawing Sheets

(56) References Cited

U.S. PATENT DOCUMENTS 6,184,517 B1 2/2001 Sawada et al.
2007/0164003 A1* 7/2007 Takamura .............. G01N 21/67
219/121.5

FOREIGN PATENT DOCUMENTS

JP 2010-197358 A 9/2010
JP 2011-180045 A 9/2011

* cited by examiner

FIG. 5
|  | Average Emission Intensity of Lead (405.78 nm) (Given Unit) | Coefficient of Variation of Emission Intensity of Lead (405.78 nm) (%) |
| --- | --- | --- |
| Flow Channel 100 (Fig. 1A) (Present Invention) | 25000 | 1.0 |
| Flow Channel 200 (Fig. 3A) (Comparison Target) | 19800 | 16.8 |
| Flow Channel 300 (Fig. 4A) (Comparison Target) | 420 | 2.1 |
FIG. 6A
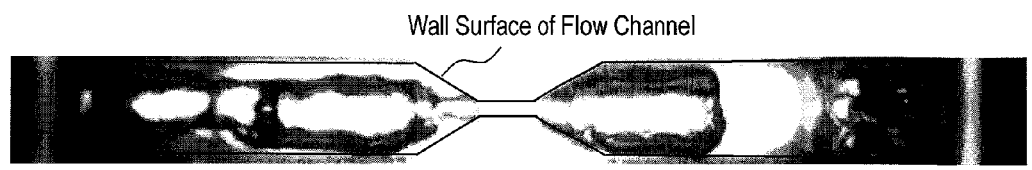
Wall Surface of Flow Channel
FIG. 6B
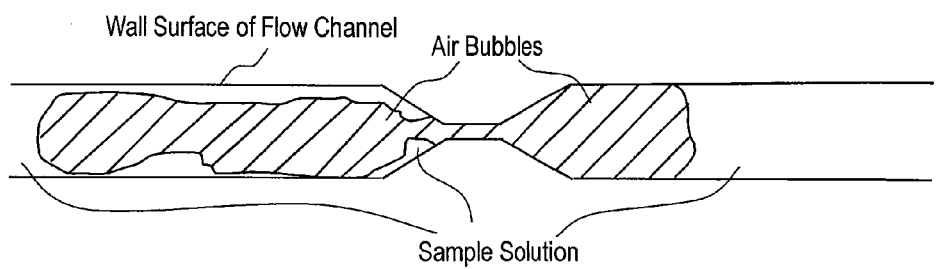
Wall Surface of Flow Channel
Air Bubbles
Sample Solution

FIG. 8
Coefficient of Variation of Emission Intensity of Lead (405.78 nm) (%)
| Flow Rate (µL/min) | 1000 | 300 | 1000 |
|---|---|---|---|
| Inter-Pulse Duration (msec) | 1000 | 1000 | 120 |
| Horizontal | 1.0 | 9.9 | 11.4 |
| Vertical | 2.9 | 3.9 | 4.6 |
FIG. 9A
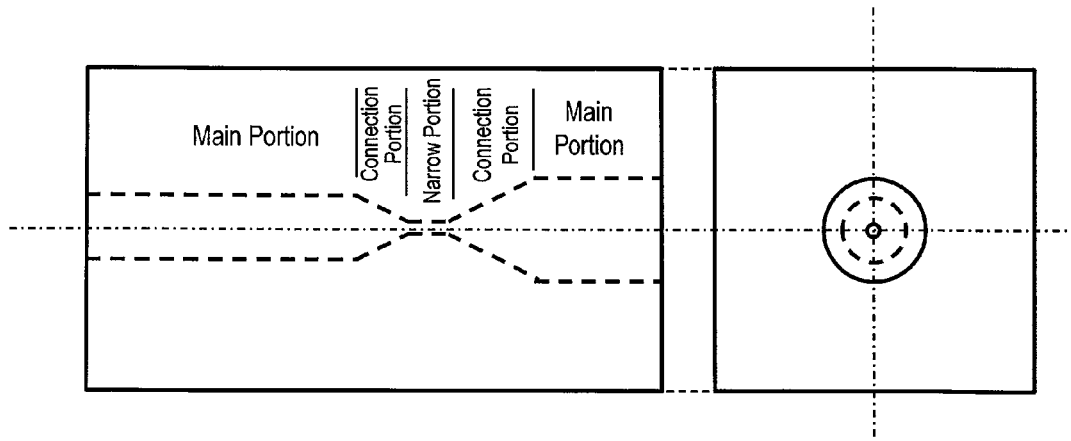
FIG. 9B
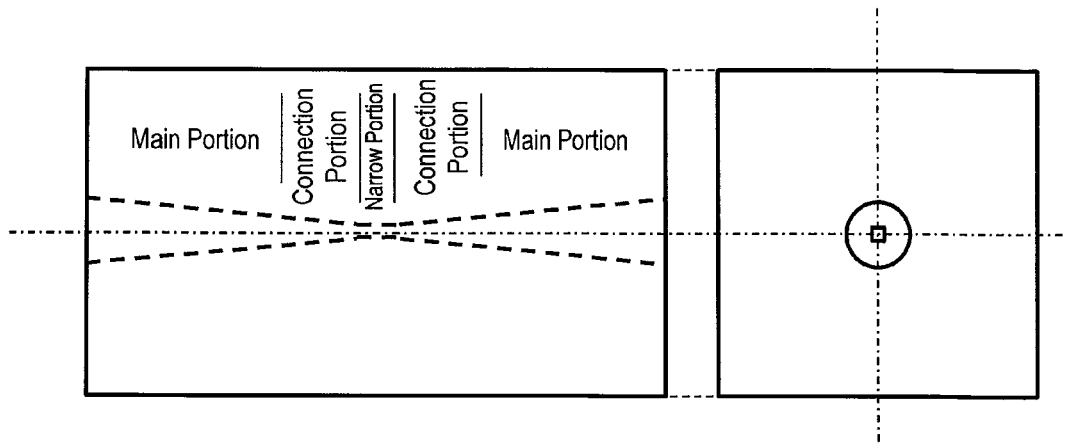

Coefficient of Variation of Emission Intensity of Lead (405.78 nm) (%)

| | |
|---|---|
| Horizontal | 7.1 |
| Vertical (When Upper Electrode is Positive Electrode) | 2.9 |
| Vertical (When Upper Electrode is Negative Electrode) | 1.9 |

PLASMA SPECTROMETER

TECHNICAL FIELD

The present invention relates to a plasma spectrometer for analyzing a liquid sample using plasma emission.

BACKGROUND ART

JP 3932368 B (Patent Literature 1) is given as the background art of the present invention. Patent Literature 1 describes a method for generating plasma and a method for elemental analysis, each comprising the steps of providing a narrow portion in a flow channel made of an insulation material, the narrow portion having a cross-sectional area markedly smaller than a cross-sectional area of the flow channel; filling the flow channel and the narrow portion with a conductive liquid, and thereafter applying an electric field to the narrow portion, to conduct the electric field through the narrow portion, thereby generating plasma at the narrow portion. Patent Literature 1 also describes an apparatus for generating plasma, the apparatus for generating plasma comprising a narrow portion in a flow channel made of an insulation material, the narrow portion having a cross-sectional area markedly smaller than a cross-sectional area of the flow channel; and a means of applying an electric field to the narrow portion to conduct the electric field through the narrow portion; and an apparatus for emission spectroscopic analysis comprising the apparatus for generating plasma.

CITATION LIST

Patent Literature

Patent Literature 1: JP 3932368 B

SUMMARY OF INVENTION

Technical Problem

Patent Literature 1 describes, in relation to a flow channel and a narrow portion that has a cross-sectional area markedly smaller than a cross-sectional area of the flow channel, the sizes of and the ratio between the cross-sectional areas of the flow channel and the narrow portion. Patent Literature 1 also describes an embodiment of a planar flow channel in which the depths of the narrow portion and the main portion of the flow channel and the flow channel of the connection portion are constant.

Patent Literature 1 does not describe a flow channel with a three-dimensional expansion in which the depths of the narrow portion, the connection portion, and the main portion of the flow channel are not constant. However, as a result of study, it has been found that in a flow channel with a three-dimensional expansion in which the depth and the width of the flow channel increase from the narrow portion through the connection portion to the main portion of the flow channel, the intensity of plasma emission is advantageously increased than when a planar flow channel with a constant depth is used, while the flow channel with a three-dimensional expansion has a problem in the phenomenon reproducibility as the behavior of air bubbles and plasma is unstable. Thus, the present invention provides a plasma spectrometer with significantly improved detection sensitivity, detection accuracy, and phenomenon reproducibility by defining the shape of a flow channel with a three-dimensional expansion and thus significantly improving the phenomenon reproducibility.

Patent Literature 1 fails to describe the arrangement direction of the flow channel. However, it has been found that the arrangement direction of a flow channel has large influence on the phenomenon reproducibility under the measurement condition of a low flow rate of a sample solution or short voltage application intervals that is advantageous when a very small amount of sample is handled, in particular. Further, it has been found that the arrangement direction of a flow channel has large influence on the phenomenon reproducibility under the condition of, in particular, low phenomenon reproducibility. Thus, the present invention provides a plasma spectrometer with significantly improved detection sensitivity, detection accuracy, and reproducibility by appropriately defining the arrangement direction of the flow channel and thus improving the phenomenon reproducibility.

Patent Literature 1 neither describes performing measurement at positions other than the narrow portion nor improving the sensitivity based on a difference in the detection position. However, as a result of study, it has been found that performing measurement at positions other than the narrow portion has influence on the detection sensitivity. Thus, the present invention provides a plasma spectrometer with significantly improved detection sensitivity by selecting a target measurement region in the flow channel.

Solution to Problem

The present invention includes a plurality of means for solving the aforementioned problem. According to one example thereof, there is provided a spectrometer for filling a flow channel having a narrow portion with a conductive liquid, applying an electrical field to the flow channel to generate air bubbles, and generating plasma in the air bubbles. A flow channel is used in which connection portions each connecting the narrow portion to one of main portions of the flow channel are substantially conical in shape, and the main portions of the flow channel are substantially cylindrical in shape.

According to another example, there is provided a spectrometer for filling a flow channel with a conductive liquid, applying an electrical field to the flow channel to generate air bubbles, and generating plasma in the air bubbles. The flow channel is arranged substantially in parallel with a vertical line.

According to still another example, there is provided a spectrometer for filling a flow channel having a narrow portion with a conductive liquid, applying an electrical field to the flow channel to generate air bubbles, and generating plasma in the air bubbles. A region adjacent to the narrow portion of the flow channel is a measurement target region.

Advantageous Effects of Invention

According to the present invention, it is possible to, in a method of generating electrical discharge in a sample solution and performing analysis using light emission in plasma thereof, improve the detection sensitivity, detection accuracy, and phenomenon reproducibility by increasing the emission intensity and thus improving the reproducibility.

Other problems, configurations, and advantageous effects will become apparent from the following description of embodiments.

BRIEF DESCRIPTION OF DRAWINGS

FIG. 5 is a diagram showing the relationship among the difference in the flow channel, the average emission intensity of lead and coefficients of variation.

FIG. 6A is a diagram showing a view of the inside of a flow channel of a plasma spectrometer of the present invention.

FIG. 6B is a diagram illustrating FIG. 6A.

FIG. 8 is a diagram showing coefficients of variation of the emission intensity of lead.

FIG. 9A is a diagram showing an exemplary flow channel.
FIG. 9B is a diagram showing an exemplary flow channel.

DESCRIPTION OF EMBODIMENTS

Figure 1A:
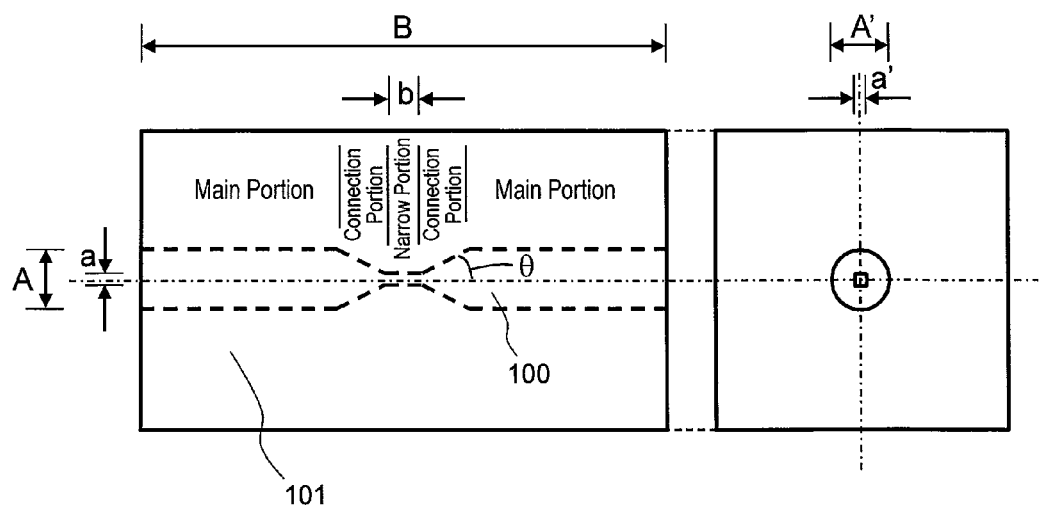
FIG. 1A is a diagram showing an exemplary flow channel of a plasma spectrometer of the present invention.

The emission intensity of plasma will change depending not only on the applied voltage level or the voltage application time but also on the shape of a flow channel, the arrangement of electrodes, the composition of a sample solution, and the like. Thus, it is generally difficult to identify the conditions to generate plasma. However, the voltage to be applied is desirably greater than or equal to 500 V, more desirably, greater than or equal to 1 kV, further desirably, greater than or equal to 1.2 kV, and still further desirably, greater than or equal to 1.5 kV. The voltage application time is desirably greater than or equal to 0.1 millisecond, more desirably, greater than or equal to 1 millisecond, further desirably, greater than or equal to 5 milliseconds, and still further desirably, greater than or equal to 20 milliseconds.

A sample solution should be electrically conductive, and acids that are used in typical elemental analysis, for example, nitric acid is suitable. Besides, a variety of acids, such as hydrochloric acid or sulfuric acid, can also be used. Further, a solution containing electrically conductive salts can also be used.

An appropriate size of a flow channel will change depending not only on the applied voltage level or the voltage application time but also on the arrangement of electrodes, the composition of a sample solution, and the like. Thus, it is generally difficult to identify an appropriate size of the flow channel. However, the length of the flow channel in the voltage application direction is about 1 to 300 mm, desirably, about 3 to 20 mm, or more desirably, about 5 to 15 mm.

The "flow channel" as referred to herein is created using an insulating material, and has a shape with closed flow channel cross-sections. Herein, a flow channel through which a liquid flows only in one direction at a given point in time is considered. In the present invention, light emission is generated using electrodes and applying a voltage thereto. Thus, when the positions of the electrodes in the flow channel are clearly known, it is possible to regard the flow channel between the electrodes as a substantial flow channel range and regard the positions of the electrodes as the opposite ends of the flow channel.

In the present invention, a flow channel with a narrow portion is handled, and the flow channel also has a portion with a larger flow channel cross-section than the narrow portion due to the significance of the narrow section. Such a portion is called a main portion of the flow channel. In addition, a portion that connects the narrow portion and the main portion of the flow channel is called a connection portion of the flow channel. Herein, a spectrometer in which a narrow portion is located at a position other than the ends of the flow channel is supposed. Therefore, the connection portion of the flow channel and the main portion of the flow channel are provided on each of the flow upstream side and the flow downstream side of the narrow portion. It is generally difficult to define the boundary between the connection portion and the main portion of the flow channel. However, the connection portion of the flow channel refers to a portion in which the flow channel expands from the narrow portion toward the main portion of the flow channel, while the main portion of the flow channel refers to a portion in which the flow channel does not expand almost at all. When the boundary between the connection portion of the flow channel and the main portion of the flow channel cannot be clearly identified in terms of the above definition, it is also possible to regard that a portion in which the width of the flow channel expands up to about three times that of the narrow portion as the connection portion of the flow channel, and regard a portion that is away from the narrow portion more than that as the main portion of the flow channel. The connection portion and the main portion are located on each of the upstream and downstream sides of the flow channel. However, a shape that is defined in an example of the present invention applies to the connection portion and the main portion on at least one of the upstream side or the downstream side. Needless to say, the shape defined in the present invention can also be applied to the connection portion and the main portion on each of the upstream side and the downstream side.

An example of the present invention is directed to not a planar flow channel in which the depths of a narrow portion, a connection portion, and a main portion of the flow channel are constant but a flow channel with a three-dimensional expansion in which both the depths and the widths of a connection portion and a main portion are increased as compared to those of a narrow portion. An example of the most appropriate flow channel shape is a flow channel in which a connection portion that connects a narrow portion to a main portion of the flow channel is substantially conical in shape, and the main portion of the flow channel is substantially cylindrical in shape.

As a conical shape of the connection portion of the flow channel, a conical shape having a half apex angle of about 10° to 80° is appropriate. If the angle is too far from such a range, the behavior of air bubbles that are generated from the narrow portion and spread to the opposite sides thereof would become unstable, with the result that phenomenon reproducibility would decrease. In addition, a connection portion that is substantially conical in shape refers to, if a perfect cone shape cannot be provided, a shape with a certain high degree of axial symmetry, such as an elliptical conical shape or a polygonal conical shape. When the axial symmetry is high, the behavior of air bubbles can be stable, which leads to high phenomenon reproducibility. When the shape of the connection portion is difficult to discriminate, it is possible to substantially regard, in each flow channel cross-section that is perpendicular to the center axis of the connection portion, a shape whose ratio of the longest line segment to the shortest line segment, which pass through the center, is less than or equal to 2:1, as a conical shape, which is desirable as a certain degree of phenomenon reproducibility is maintained.

A main portion of the flow channel that is substantially cylindrical in shape refers to a shape of the main portion that has, when a perfect cylindrical shape cannot be provided, high axial symmetry, is straight, and has no change in the cross-section, such as an elliptical column or a polygonal column. When the main portion has such a shape, the behavior of air bubbles that are generated from the narrow portion and spread to the main portion can be more stable, with the result that phenomenon reproducibility can be improved. Further, such a shape also has the advantageous effect that the phenomenon reproducibility is maintained as the generated air bubbles will be cleanly removed from the flow channel upon transfer of a liquid, and thus the air bubbles will not remain when a voltage is applied next time. In particular, in view of removing air bubbles, the main portion desirably has no change in the shape or the cross-section. Even if the main portion has a change in the shape or the cross-section, the change rate of the area of the flow channel cross-section, which is perpendicular to a line that connects the center line of the main portion, is desirably less than or equal to 2 times. Air bubbles are likely to accumulate in a portion, which has a large cross-sectional area, of the main portion of the flow channel. Thus, when the cross-sectional area changes, the largest cross-sectional area is desirably located not close to the narrow portion but around an end of the flow channel that has little influence on the light emission. In addition, in view of removing air bubbles, the main portion of the flow channel is desirably as straight as possible, and even when the main portion is not perfectly straight, no problem would arise as long as the curve of the line that connects the center of the main portion of the flow channel has an angle that is less than or equal to 60°. In view of the stability of when air bubbles grow, the center axis of the narrow portion desirably coincides with that of the main portion. However, even if they deviate from each other, the phenomenon reproducibility can be sufficiently high as long as the ratio of the amount of deviation to the width of the flow channel cross-section of the main portion in the direction of the deviation is less than or equal to ½.

In order to remove the generated air bubbles through transfer of a liquid, the flow channel cross-section of the main portion of the flow channel is desirably about the same size as or smaller than the size of the generated air bubbles or half the volume of the generated air bubbles so that the generated air bubbles can be removed through transfer of a liquid. As a result of study, it has been found that the typical size of air bubbles is about 10 µL. In consideration of the diameter of the corresponding sphere, the maximum width of the flow channel cross-section is desirably less than or equal to about 2.7 mm.

Meanwhile, when the width of the flow channel in the vertical direction is greater than that in the horizontal direction, there may be cases where the generated air bubbles flow up in the flow channel, and thus are not sufficiently washed away. Thus, the width of the main portion of the flow channel in the vertical direction is desirably about the same size as or smaller than that in the horizontal direction.

In an example of the present invention, in regard to the arrangement direction of the flow channel, the flow channel is arranged substantially in parallel with the vertical direction. This is because the generated air bubbles will be removed through transfer of a liquid most naturally due to the buoyancy effect, so that the phenomenon reproducibility is maintained. Such an arrangement has a prominent effect, in particular, under the conditions that are disadvantageous in maintaining the phenomenon reproducibility such that the amount of a transferred liquid is small and the voltage application intervals are short. The most desirable configuration is that a flow channel be straight, and a straight line that passes though the center of the flow channel be arranged in parallel with the vertical line. Practically, as long as the internal angle between the line that passes through the center of the flow channel and the vertical line is less than or equal to 60°, sufficient buoyancy will act upon the air bubbles, having the effect of maintaining the phenomenon reproducibility. It is also important to arrange the narrow portion in parallel with the vertical direction. In such a case also, as long as the interior angle between the narrow portion and the vertical line is less than or equal to 60°, sufficient buoyancy will act upon the air bubbles, having the effect of maintaining the phenomenon reproducibility. In any case, the movement direction of a fluid is desirably set in the direction from the lower side of the vertical direction to the upper side of the vertical direction. In regard to the polarity of each electrode, as the amount of air bubbles that are generated on the negative electrode side is larger than that on the positive electrode side, it is desirable to use the electrode on the upper side of the vertical direction as the negative electrode and use the electrode on the lower side of the vertical direction as the positive electrode so as to avoid entry of air bubbles, which have been generated on the negative electrode side, into the flow channel.

In an embodiment of the present invention, measurement is desirably performed in a region that is adjacent to the narrow portion of the flow channel. This is because in the connection portion on the positive electrode side that is adjacent to the narrow portion of the flow channel, atomic emission is as strong as or stronger than that in the narrow portion, and the intensity ratio of the atomic emission to the background light is the maximum. In particular, the intensity ratio of the atomic emission to the background light is the maximum at a portion, which does not include an extension of the narrow portion, in the connection portion. When measurement is performed in such regions, measurement with high detection sensitivity becomes possible.

Embodiments of the present invention will be hereinafter described with reference to the drawings.

Embodiments

[Embodiment 1]

This embodiment will describe an example of a plasma spectrometer.

FIG. 1A is a diagram illustrating an example of a flow channel 100 of a plasma spectrometer in this embodiment. The flow channel 100 is a flow channel having widths A and A' and an overall length B, and having a narrow portion with widths a and a' and a length b at the center. The narrow portion, the connection portions, and the main portions of the flow channel are displayed altogether. The widths a and a' of the narrow portion are narrower than the width A of the flow channel, and is desirably less than or equal to ⅓, or further desirably, less than or equal to ⅕ the width A of the flow channel. The length b of the narrow portion is shorter than the overall length B of the flow channel 100, and is desirably less than or equal to ⅕, or further desirably, less than or equal to 1/10 the overall length B of the flow channel 100. The overall length B of the flow channel is desirably greater than or equal to 1 mm and less than or equal to 300 mm.

The present invention is directed to not a planar flow channel in which the depths of a narrow portion, connection portions, and main portions of the flow channel are constant but a flow channel with a three-dimensional expansion in which both the depths and the widths of connection portions and main portions are increased as compared to those of a narrow portion. An example of the most appropriate flow channel shape is a flow channel in which a connection portion leading from a narrow portion to a main portion of the flow channel is substantially conical in shape, and the main portion of the flow channel is substantially cylindrical in shape. The widths A and A' are desirably substantially equal. Herein, a flow channel having a main portion with a perfect circle cross-section was used, and the widths A and A' were set to 1.6 mm. For the cross-section of the narrow portion, a square cross-section was used, and the widths a and a' were set to 0.2 mm. When not a roundish cross-sectional shape like a cylinder but a square cross-section with straight sides is adopted, there is an advantage in that measurement of light emission from the inner side of the narrow portion becomes easier. The length b of the narrow portion was set to 0.64 mm.

The connection portion for connecting the narrow portion to a portion, which has the widths A and A', of the main portion of the flow channel was formed in a conical shape having a half apex angle θ of 27°, which is the angle from the center axis that penetrates the narrow portion so that the center axes that penetrate the narrow portion, the connection portion of the flow channel, and the main portion of the flow channel coincided with one another. When the angle is represented by the apex angle of a cone, it is represented as 54°. When a shape that is symmetrical about the center axis is selected as describe above, it becomes possible to improve the phenomenon reproducibility of the plasma emission phenomenon. As such a connection portion can be produced only by processing a flow channel, for example, by opening a hole in the flow channel with a drill from a plane at an end of the flow channel of a material and polishing it, there is an advantage in that the processing cost can be reduced than those of other complex structures. The apex angle of the cone may be any angle as long as it is not a too acute angle. For example, the angle may be in the range of a half apex angle of about 10° to 80°.

As a material for forming the flow channel, an insulating material that has light-transmitting performance with respect to light at a measurement target emission wavelength and has resistance to, in particular, acids of all chemicals is desirably used. For example, a variety of optical glass, resin for optical components, and the like can be adopted. In this embodiment, quartz glass 101 with a high UV-transmitting property and high shock resistance was used as the material of the flow channel.

Figure 1B:
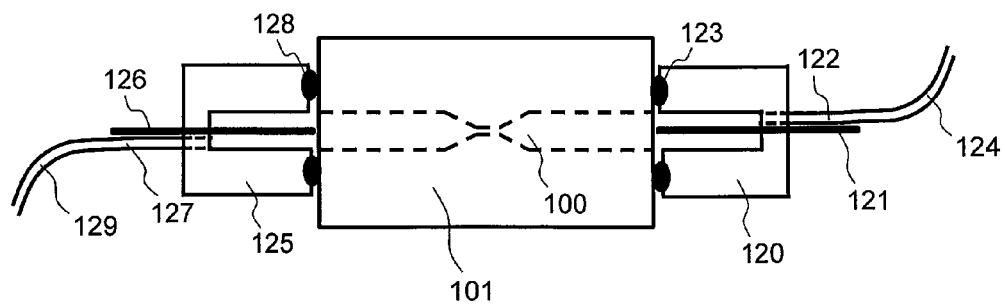
FIG. 1B is a diagram showing an exemplary arrangement of a flow channel, electrodes, and connectors.

FIG. 1B is a diagram illustrating an example of the relationship among the flow channel 100, electrodes, connectors, and pipes. At the right side end of the flow channel 100, a connector 120 is connected to the quartz glass 101 via an O-ring 123 using a pressure method to avoid leakage of liquid that would occur when the liquid is flowed from the outside. An electrode 121 and a pipe connection port 122 are fixed to the connector 120. A pipe 124 is connected to the pipe connection port 122. In this embodiment, a platinum wire with a diameter of 0.5 mm was used as the electrode 121. A tip end of the electrode 121 is arranged such that it is located at an end of the flow channel 100. A cavity in the connector 120 is a portion through which a liquid such as a sample solution passes, and desirably has a structure that is connected directly from the end of the flow channel and has the same diameter as the flow channel so as to facilitate passage of air bubbles and the like. Herein, the diameter of the cavity in the connector 120 was set to 1.6 mm. In addition, Teflon was used as the material of the connector 120. As with the right side end of the flow channel 100, an O-ring 128, a connector 125, an electrode 126, a pipe connection port 127, and a pipe 129 are also arranged at the left side end. The electrodes 121 and 126 are located at the centers of the connectors 120 and 125, respectively, and lines that connect the respective electrodes and the narrow portion are straight lines.

Figure 2:
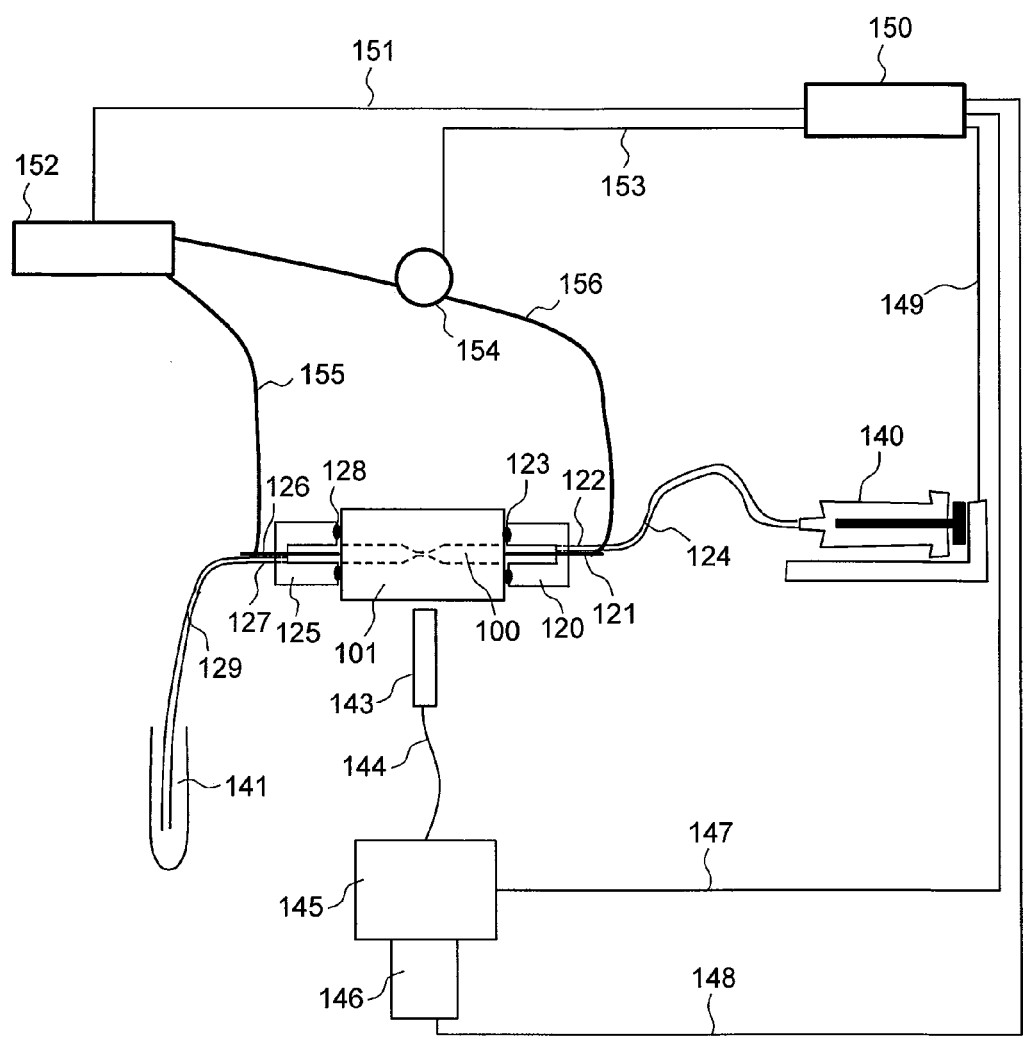
FIG. 2 is a diagram showing an exemplary overall configuration of a plasma spectrometer.

FIG. 2 is a schematic diagram showing an exemplary configuration of the plasma spectrometer in this embodiment. Description of the connection around the flow channel 100 will be omitted as it is shown in FIG. 1B. A syringe pump 140 is connected to the pipe 124. By controlling the syringe pump 140, it is possible to transfer a solution in the syringe pump 140 to the flow channel 100. The syringe pump 140 is connected to a computer 150 via a signal line 149, so that the operation thereof is controlled by the computer 150. A waste liquid container 141 is arranged at an end of the other pipe 129.

The electrodes 121 and 126 are connected to a power supply 152 via high-voltage cables 155 and 156, respectively. In this embodiment, a DC pulse power supply was used as the power supply 152. An ammeter 154 for measuring current is connected in series with the high-voltage cable 156. The computer 150 is connected to the power supply 152 via a signal line 151, and can set the output voltage of the power supply 152 and control the on/off timing using a trigger on the basis of input information. In addition, the computer 150 is connected to the ammeter 154 via a signal line 153, and captures the measurement data of the ammeter 154 and further performs information processing on the measurement data, so that the data can be used to control the power supply 152.

An optical fiber end 143 is one end of an optical fiber 144, and is arranged toward the flow channel 100. The other end of the optical fiber 144 is connected to a spectroscope 145. Light that is received by the optical fiber end 143 is input to the spectroscope 145 via the optical fiber 144 and is subjected to spectral observation. The spectroscope 145 is connected to the computer 150 via a signal line 147 so that the spectroscope 145 can be controlled from the computer 150.

An imaging device 146 such as a CCD camera is connected as a detector to the spectrometer 145, and receives light spectrally observed by the spectrometer 145. The imaging device 146 is connected to the computer 150 via a signal line 148 so that the imaging device 146 can be controlled from the computer 150. Information on the spectrum measured by the imaging device 146 can be recorded on a storage device in the computer 150 and subjected to information processing. Data related to the light emission, in combination with data on a temporal change of current, which has been measured with the ammeter 154 and recorded on the recording device of the computer 150, can be processed by the computer 150. As described above, the computer 150 has the function of the control unit and the function of the arithmetic unit at the same time.

The procedures to supply as a sample solution a decinormal nitric acid solution containing 100 ppm lead to the flow channel in the plasma spectrometer shown in FIGS. 1A, 1B and 2, and apply a voltage thereto to measure light emission are described below. Among emission spectra measured by the imaging device 146 via the spectroscope 145, an emission spectrum of an emission line derived from lead (405.78 nm) was focused, and a net emission intensity obtained by subtracting the background light intensity from the intensity of the emission spectrum was measured as the emission intensity derived from lead. It should be noted that the solution containing lead was used as the sample solution herein only for illustration purposes. Thus, a solution containing other elements can also be analyzed through similar procedures, so that a similar phenomenon and advantageous effects can be observed.

Water was first introduced into the flow channel 100 that is empty, and then, decinormal nitric acid was flowed to clean the flow channel 100. First, water was poured into a syringe of the syringe pump 140, and then, the syringe pump 140 was moved in accordance with an instruction from the computer 150, so that the water was flowed into the flow channel 100 via the pipe 124, the pipe connection port 122, and the inside of the connector 120 to clean the flow channel 100, and then, the water having cleaned the flow channel 100 was collected into the waste liquid container 141 via the inside of the connector 125, the pipe connection port 127, and the pipe 129 on the downstream side. Next, decinormal nitric acid was flowed in accordance with similar procedures to clean the flow channel 100.

Next, a decinormal nitric acid solution containing 100 ppm lead was poured as a sample solution into the flow channel 100 in accordance with similar procedures to conduct light emission with the application of a voltage. An appropriate voltage applied herein is desirably greater than or equal to 500 V, more desirably, greater than or equal to 1 kV, further desirably, greater than or equal to about 1.2 kV, and still further desirably, greater than or equal to 1.5 kV. The voltage application time is desirably greater than or equal to 0.1 millisecond, more desirably, greater than or equal to 1 millisecond, further desirably, greater than or equal to 5 milliseconds, and still further desirably, greater than or equal to 20 milliseconds. Herein, the applied voltage was set to 1.5 kV, and the pulse width of the applied voltage was set to 5 milliseconds.

In this embodiment, the polarity of the power supply 152 was set so as to apply a positive high voltage to the high-voltage cable 155 and apply the ground potential to the high-voltage cable 156. That is, the polarity of the electrode was set so that the electrode 121 on the upstream side of the transferred sample solution became a negative electrode while the electrode 126 on the downstream side of the transferred sample solution became a positive electrode. The relationship between the polarities of the electrodes and the direction of the flow of the sample solution are not limited to such combination, and may be an opposite combination.

The computer 150 generates a voltage application start signal. The power supply 152, upon receiving the signal from the computer 150, applies a voltage to the flow channel 100 in accordance with the signal. Exposure control of the imaging device 146 was performed by inputting a signal, which is similar to a voltage application signal, to the imaging device 146 from the computer 150. Measurement of current with the ammeter 154 was performed by outputting a signal, which is synchronized with the voltage application start signal transmitted to the power supply 152, from the computer 150, and inputting the signal as a signal to the ammeter 154.

In the plasma spectrometer that uses the flow channel 100 shown in FIGS. 1A and 1B, emission intensity that is far higher than that of the conventional plasma spectrometer is obtained, and an analysis result in which the coefficient of variation of the emission intensity is about 1%, which shows quite high reproducibility as the electrostatic discharge measurement, can be obtained. For comparison purposes, a result obtained by measuring the light emission of lead using two flow channels, which differ from those in FIGS. 1A and 1B, in the same way are described below.

Figure 3A:
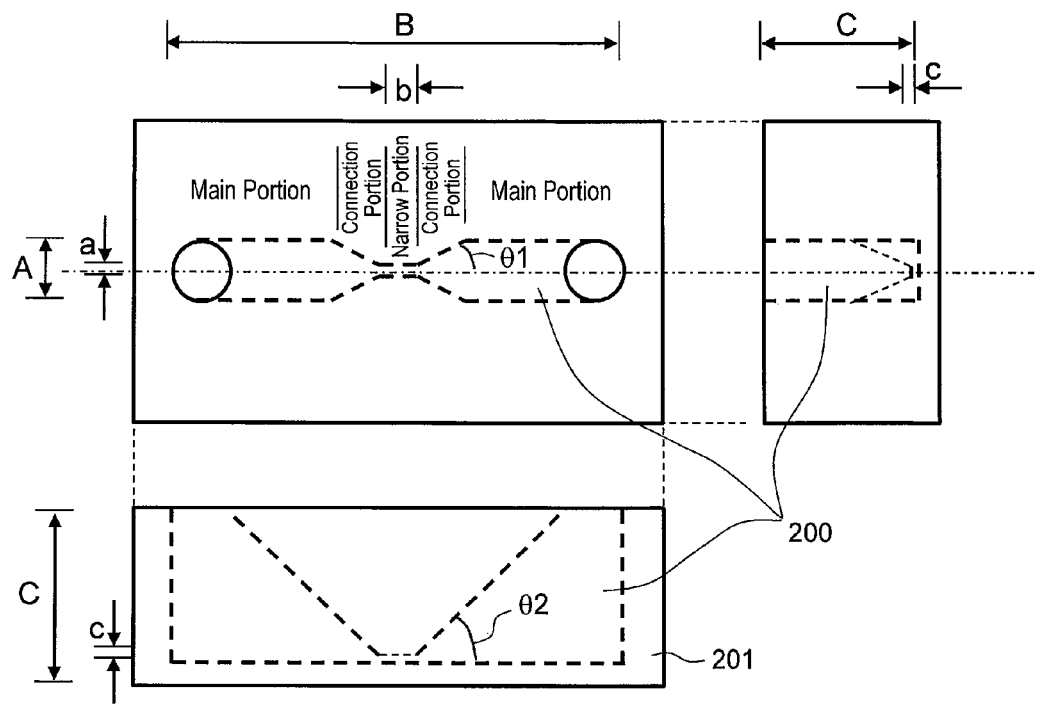
FIG. 3A is a diagram showing an exemplary flow channel as a comparison target.

FIG. 3A is a diagram illustrating an example of a flow channel 200 as a comparison target. The flow channel 200 is a flow channel that is created in quartz glass 201, has a width A, an overall length B, and a height C, has a narrow portion with widths a and c and a length b at the center, and has connection angles θ1 and θ2. The narrow portion, the connection portions, and the main portions of the flow channel are displayed altogether. Herein, the width A is 1.6 mm, the overall length B is 10.5 mm, and the height C is 5 mm. The cross-section of the narrow portion has widths a and c of 0.1 mm, and a length b of 0.5 mm. The angles θ1 and θ2 of the connection portion are 45°. The flow channel 200 is not a planar flow channel in which the depths of a narrow portion, connection portions, and main portions of the flow channel are constant but a flow channel with a three-dimensional expansion in which both the depths and the widths of connection portions and main portions are increased as compared to those of a narrow portion as with the flow channel 100. However, shown herein is an example of a flow channel shape in which the symmetry of expansion is low and each main portion of the flow channel also has a shape with a low axial symmetry. When this is described with the bottom diagram of FIG. 3A, the flow channel in the connection portion expands only upward in the vertical direction, and does not expand downward. That is, the flow channel obviously has an asymmetrical shape. In addition, the shape of the flow channel cross-section of each main portion of the flow channel leading toward a round hole at an end of the flow channel is irregular and is not a shape like a cylinder or a polygonal column that has high symmetry, is straight, and has no change in the cross-sectional area.

Figure 3B:
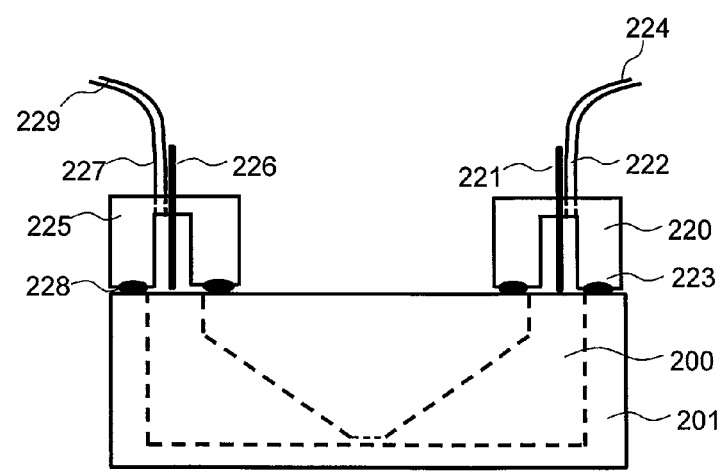
FIG. 3B is a diagram showing an arrangement of a flow channel as a comparison target, electrodes, and connectors.

FIG. 3B is a diagram illustrating an example of the relationship among the flow channel 200, electrodes, connectors, and pipes. At the right side end of the flow channel 200, a connector 220 is connected to the quartz glass 201 via an O-ring 223, and an electrode 221 and a pipe connection port 222 are fixed to the connector 220. A pipe 224 is connected to the pipe connection port 222. An end of the electrode 221 is arranged so as to be located at an end of the flow channel 200. As with the right side end of the flow channel 200, an O-ring 228, a connector 225, an electrode 226, a pipe connection port 227, and a pipe 229 are also arranged at the left side end. The electrodes 221 and 226 are located at the centers of the connectors 220 and 225, respectively. It is seen that unlike the flow channel 110 shown in FIGS. 1A and 1B, a line that connects the center of the flow channel 200 is not a straight line but a curved line with a large angle. The flow channel cross-sectional area of each main portion of the flow channel changes by five times or more, which exhibits a high change rate.

Figure 4A:
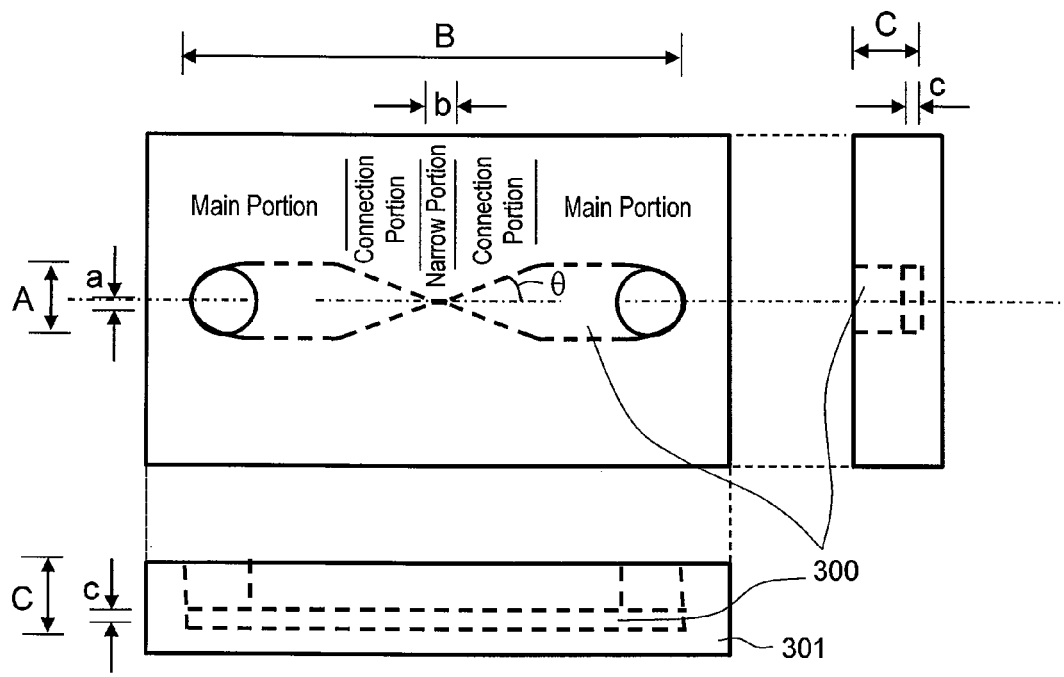
FIG. 4A is a diagram showing an exemplary flow channel as a comparison target.

FIG. 4A is a diagram showing another example of a flow channel 300 as a comparison target. The flow channel 300 is a flow channel that is created in quartz glass 301, and has a width A, an overall length B, a height C, has a narrow portion with a width a and a length b at the center, and has a connection angle θ. The flow channel has a uniform depth c, and has a height C including the connection portions. The narrow portion, the connection portions, and the main portions of the flow channel are displayed altogether. Herein, the width A is 3 mm, the overall length B is 10.5 mm, and the height C is 2 mm. The width a of the cross section is 0.1 mm, and the length b thereof is 0.4 mm. The angle θ of the connection portion is 45°, and the depth c of the flow channel is 0.08 mm. The flow channel 300 is also a flow channel having a narrow portion at the center like the flow channel 100, but is a flow channel with a planar structure in which the depth of the flow channel is constant at portions excluding the portions connected to the connecters.

Figure 4B:
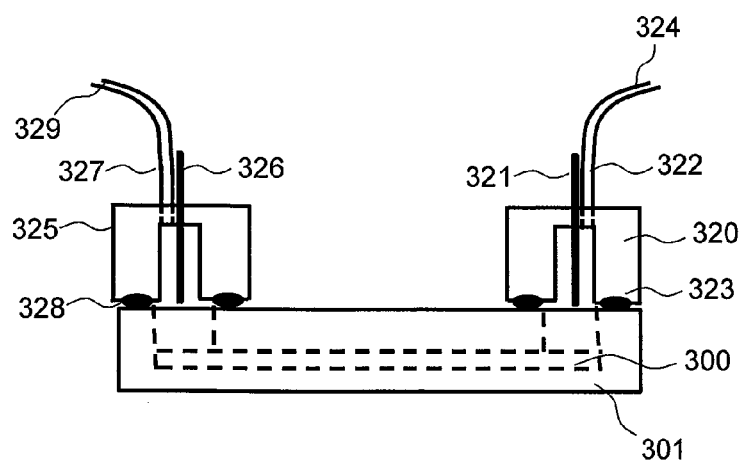
FIG. 4B is a diagram showing an arrangement of a flow channel as a comparison target, electrodes, and connectors.

FIG. 4B is a diagram illustrating an example of the relationship among the flow channel 300, electrodes, connectors, and pipes. At the right side end of the flow channel 300, a connector 320 is connected to the quartz glass 301 via an O-ring 323, and an electrode 321 and a pipe connection port 322 are fixed to the connector 320. A pipe 324 is connected to the pipe connection port 322. An end of the electrode 321 is arranged so as to be located at an end of the flow channel 300. As with the right side end of the flow channel 300, an O-ring 328, a connector 325, an electrode 326, a pipe connection port 327, and a pipe 329 are also arranged at the left side end. The electrodes 321 and 326 are located at the centers of the connectors 320 and 325, respectively.

FIG. 5 shows an example of the measurement results of the light emission of lead performed in the same way by replacing portions corresponding to FIG. 1B in the plasma spectrometer in FIG. 2 with those in FIGS. 3B and 4B. When the average light emission intensities of lead are compared, it is found that the light emission intensity is the highest when the flow channel 100 is used; high to about the same degree when the flow channel 200 is used; and low when the flow channel 300 is used. Each of the flow channels 100 and 200 is a flow channel with a three-dimensional expansion that expands from the narrow portion to the main portions of the flow channel, while only the flow channel 300 is a planar flow channel with a uniform depth. Thus, a large difference in the measured emission intensity is considered to be due to such difference in the flow channel structure. In regard to the flow channel 100 and the flow channel 200, the facts that the degree of concentration of an electric field around the narrow portion is higher than that of the flow channel 300 and that the substantial volume of the generated plasma is large as the volume of the generated gas is large are estimated to be the reasons why the plasma emission intensity is high. That is, the use of a flow channel that expands three-dimensionally from the narrow portion to the main portions of the flow channel has the significant effect of increasing the emission intensity, and thus can be said to be an effective method for increasing the detection intensity.

Next, when the coefficients of variation of the respective measured emission intensities of lead are compared, it is found that the coefficient of variation is the lowest when the flow channel 100 is used; small to about the same degree when the flow channel 300 is used; and extremely high when the flow channel 200 is used. Herein, the coefficient of variation refers to a value obtained by dividing the standard deviation of the emission intensity by the average value of the emission intensity. A small coefficient of variation means high phenomenon reproducibility, which is thus desirable for an analysis method. In terms of only improving the emission intensity, there is no difference in using the flow channel 100 or the flow channel 200. However, it is found that the flow channel 200 has a big problem in that it has low phenomenon reproducibility.

The flow channel 100 is a straight flow channel with high axial symmetry in which each connection portion of the flow channel is conical in shape and each main portion is cylindrical in shape, while the flow channel 200 is a flow channel that has an irregular cross-sectional shape of the flow channel, has low axial symmetry, is curved, and has a large change in the cross-sectional area. Such difference in the flow channel shape is considered to be a reason why the coefficient of variation of the emission intensity is increased, that is, why the phenomenon reproducibility is deteriorated.

FIG. 6A shows an exemplary image of the behavior of air bubbles captured with a high-speed camera when a voltage was applied to a flow channel with conical connection portions and cylindrical main portions like the flow channel 100. The width of each main portion is 1.6 mm, and the half apex angle of each connection portion is 27°. The cross-section of the narrow portion is a square, and has a width of 0.2 mm and a length of 0.64 mm. FIG. 6A is a view after a voltage of 1.6 kV was applied for 18 milliseconds. The bright portion in the image is the illuminated portion. Under such measurement conditions, plasma emission is not noticeably observed as the surrounding illumination is bright. FIG. 6B is a schematic diagram for illustrating the view in FIG. 6A. It is found that air bubbles have been generated and grown on the opposite sides of the narrow portion at the center of the flow channel. It is found that air bubbles have grown stably as compared to the example shown next, and have fully spread across the flow channel, in particular, on the right side of the drawing that corresponds to the upstream side of the flow channel, and the gas-liquid interface at the right end is also stable. Even on the left side of the flow channel, air bubbles have grown stably, and are in a stable state. As the behavior of the air bubbles is stable as described above, the reproducibility of the emission intensity is considered to be high. The volume of air bubbles estimated from this image was about 5 μL, and there was no big difference depending on the voltage application condition.

Figure 6C:
FIG. 6C is a diagram showing a view of the inside of a flow channel as a comparison target.

FIG. 6C shows an example of an image of the behavior of air bubbles captured with a high-speed camera when a voltage was applied to a flow channel that expands three-dimensionally from a narrow portion to main portions of the flow channel like the flow channel 200 but has low symmetry of expansion of connection portions, has an irregular flow channel cross-sectional shape with low axial symmetry at the main portions continuous with the connection portions of the flow channel, has a big change in the cross-sectional area of the flow channel, and is greatly curved. Each main portion has a width of 1.6 mm, an overall length of 10.5 mm, and a height of 5 mm. The cross-section of the narrow portion is a square with a width of 0.1 mm, and the length b of the narrow portion is 0.5 mm. The angle of the connection portion is 45°. FIG. 6C shows a view after a voltage of 1.6 kV was applied for 12 milliseconds. The image was captured upward from the bottom side in the arrangement shown in FIG. 3B. The bright portion in the image is not due to the light emission but due to the surrounding illumination. The image in FIG. 6C is darker than that in FIG. 6A as most portions of the illumination have been blocked by the connectors. Although a view in which stable air bubbles have been generated and grown can be seen in FIG. 6A, no clear, stable gas-liquid interface is observed in FIG. 6C, which can confirm that the gas-liquid interface is disturbed. Plasma emission will be generated with the presence of electric discharge at the gas-liquid interface of air bubbles. Thus, the formation of a stable gas-liquid interface is important to improve the phenomenon reproducibility. Meanwhile, as a flow channel configuration with low symmetry has a disturbed gas-liquid interface, the phenomenon reproducibility is low.

When the two images captured with the high-speed camera are observed in detail, it is found that when air bubbles are generated and grow, the air bubbles blow out toward the main portions of the flow channel from the narrow portion. In the case of FIG. 6A, it is seen that the blown-out air bubbles reach the main portions of the flow channel without being broken, and then, the air bubbles slowly grow in the main portions. On the left side corresponding to the positive electrode side of the narrow portion, it is seen that at the connection portion outside the narrow portion, air bubbles are not spread across the flow channel, but have a shape such that a sample solution surrounds a thin cylindrical portion of the air bubbles. However, in the case of FIG. 6C, it is seen that, as each connection portion of the flow channel has low symmetry, air bubbles that have blown out are subjected to asymmetrical force from the liquid, and thus are broken into small pieces. Therefore, it is found that the air bubbles do not grow stably, and thus the phenomenon reproducibility is low.

From the two images captured with the high-speed camera, it is also possible to observe a view in which air bubbles vibrate upon application of a voltage. Joule heat that is generated upon application of a voltage acts in the direction of increasing the size of air bubbles, whereas the flow of the liquid acts in the direction of reducing the size of air bubbles, and it is thus considered that vibration is generated due to the fluid effect inclusive of the influence of the flow channel shape. In this case, it was observed that although the generated air bubbles were not broken in FIG. 6A in which the symmetry of each of the connection portions and the main portions of the flow channel is high, air bubbles were broken in FIG. 6C in which the symmetry of the flow channel is low as asymmetric force is applied to the air bubbles upon generation of vibration. Therefore, it is found that the air bubbles do not grow stably, and thus the phenomenon reproducibility is low.

Further, in FIG. 6C, a phenomenon is also observed that when air bubbles blow out, buoyancy acts upon the generated air bubbles, which causes the air bubbles to move upward in the vertical direction, and thus, the air bubbles move to the outside of the focal range of the camera and thus disappear from the image. The fact that each main portion of the flow channel has low symmetry and is curved, which thus causes buoyancy to act upon the air bubbles in the vertical direction and thus prevents stable growth of the air bubbles is also a reason why the phenomenon reproducibility is low. In addition, it is seen that air bubbles that have been broken in the flow channel on the upstream side of the narrow portion are not washed away to the end of the flow channel during the time between voltage application pulses. As the flow channel is curved and has an inappropriate thickness, the flow of the liquid is not uniform, and a portion with a low flow velocity is generated. When air bubbles enter such portion, it is considered to be difficult to remove such air bubbles. As the air bubbles that remain in the flow channel have influence on the degree of concentration of an electric field as well as the behavior of air bubbles generated when a next voltage is applied, it is also found that the phenomenon reproducibility becomes further low each time a voltage is applied.

The volume of the generated air bubbles is usually about 0.1 to 100 µL, typically, about 1 to 10 µL, and further typically, about 5 µL. When air bubbles enter the curved portion of the flow channel, the air bubbles will not be sufficiently pushed out as a solution flows through portions other than the air bubbles in places where the cross-sectional area of the flow channel is larger than the cross-sectional area of the air bubbles. The width of the flow channel is desirably about the same as or narrower than the size of the generated air bubbles or a half the volume of the generated air bubbles. In order to increase the degree of concentration of an electric field at the narrow portion to increase the emission intensity, it is desirable to thicken the main portions of the flow channel. However, thickening the main portions may not be appropriate to achieve the objective of ensuring the phenomenon reproducibility. When air bubbles are just considered as spheres, air bubbles with volumes of 100 µL, 10 µL, 5 µL, and 2.5 µL have diameters of about 5.8 mm, 2.7 mm, 2.1 mm, and 1.7 mm, respectively. Accordingly, the maximum width of the flow channel cross-section may be desirably less than or equal to about 5.8 mm, more desirably, less than or equal to about 2.7 mm, further desirably, less than or equal to 2.1 mm, still further desirably, less than or equal to 1.7 mm. It is considered that the width of each main portion is preferably greater in view of the voltage concentration. Therefore, the width of each main portion may desirably be about less than or equal to 2.7 mm, for example. In addition, as the air bubbles have buoyancy in the vertical direction of the flow channel, and thus have a property of being likely to move away from the lower side of the flow channel in the vertical direction, it is desirable that the width of the flow channel in the vertical direction is about the same as or smaller than the width of the flow channel in the horizontal direction.

So far, it has been practically impossible to perform simulation of electrostatic discharge in air bubbles generated in a liquid, and it has also been practically impossible to associate the fluidal behavior of air bubbles and a liquid with the simulation of electrical discharge. Thus, the behavior and the size of air bubbles shown herein have been clarified for the first time from the aforementioned experimental results.

As exemplarily described in this embodiment, in a spectrometer for filling a flow channel having a narrow portion with a conductive liquid, applying an electric field to the flow channel to generate air bubbles, and generating plasma in the air bubbles, it is effective to adopt a straight flow channel structure in which each connection portion has a highly symmetrical shape like a conical shape, and each main portion of the flow channel has a highly axially symmetrical shape like a cylindrical shape and has little change in the cross-sectional area to improve the detection accuracy and reproducibility.

Although this embodiment has described an example of a specific flow channel configuration, the scope of the present invention is not limited thereto, and is also effective for other flow channel shapes.

[Embodiment 2]

This embodiment will describe an example of a plasma spectrometer in which a flow channel is arranged in parallel with the vertical line.

Figure 7:
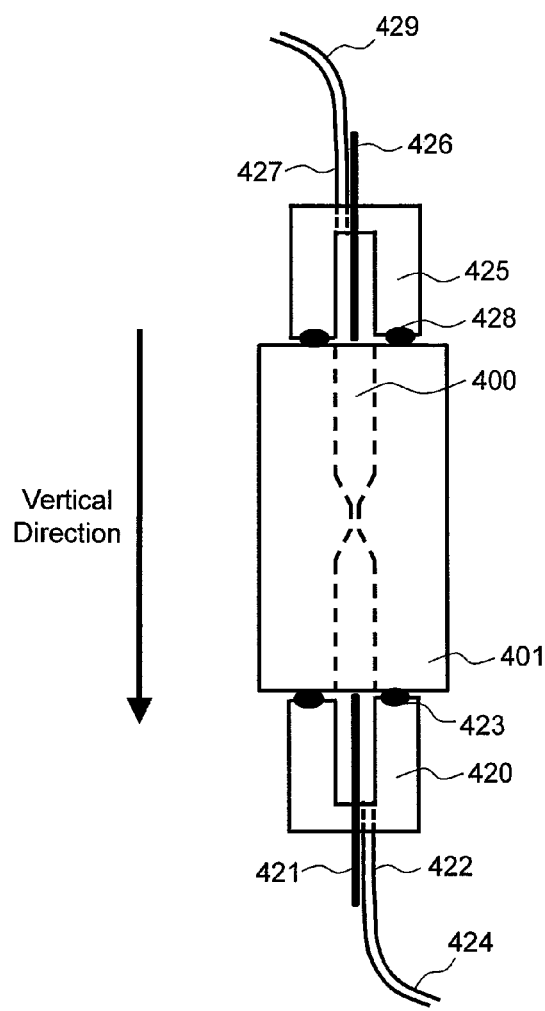
FIG. 7 is a diagram partly showing an exemplary configuration of a plasma spectrometer in which a flow channel is arranged in parallel with the vertical line.

FIG. 7 is a diagram showing an exemplary arrangement of a flow channel 400 of a plasma spectrometer in this embodiment. A flow channel 400 is a flow channel with a similar shape to the flow channel 100. The flow channel 400 is created in quartz glass 401. The flow channel 400 is arranged so that its orientation is parallel with the vertical direction. As in FIG. 1B, at the lower side end of the flow channel 400, a connector 420 is connected to the quartz glass 401 via an O-ring 423 using a pressure method to avoid leakage of liquid that would occur when the liquid is flowed from the outside. An electrode 421 and a pipe connection port 422 are fixed to the connector 420. A pipe 424 is connected to the pipe connection port 422. A tip end of the electrode 421 is arranged such that it is located at an end of the flow channel 400. As with the lower side end of the low channel 400, an O-ring 428, a connector 425, an electrode 426, a pipe connection port 427, and a pipe 429 are also arranged at the upper side end.

When plasma spectroscopy was performed, portions shown in FIG. 1B of the schematic diagram of the exemplary configuration of the plasma spectrometer shown in FIG. 2 were replaced with portions shown in FIG. 7, and the position of the optical fiber end 143 was adjusted to the position of the flow channel 400. The pipe 424 and the pipe 429 were connected to the syringe pump 140 and the waste liquid container 141, respectively, so that the liquid transfer direction of the sample solution became the direction from the lower side of the vertical direction to the upper side of the vertical direction.

When plasma is generated with the application of a pulse voltage, air bubbles are generated. In order to improve the phenomenon reproducibility for each voltage application pulse as well as the reproducibility of the emission intensity, it is important to remove as many air bubbles, which have been generated upon application of a voltage immediately before, as possible during the time between voltage application pulses. That is, in order to improve the reproducibility of the emission intensity, the volume of a sample that flows during the time between voltage application pulses may be increased by increasing the flow rate as well as the time between voltage application pulses. However, such a method has a problem in that the volume of the sample used for the analysis would increase. In particular, such a problem becomes serious when only a small volume of sample solution is analyzed. Conversely, conventionally, when only a small volume of sample solution is analyzed, it has been impossible to increase the flow rate or the time between voltage application pulses. Thus, there has been no other way but to perform analysis under conditions that are disadvantageous in removing air bubble, that is, under conditions in which the reproducibility is likely to decrease.

In the plasma spectrometer in which a flow channel is arranged in parallel with the vertical line shown in FIG. 7, it is possible to maintain high emission intensity and obtain analysis results of high reproducibility with a sufficiently small coefficient of variation of the emission intensity even under the conditions in which the amount of a sample solution used is small and the reproducibility is thus likely to decrease. For comparison purposes, the measurement results of light emission that were obtained by arranging the flow channel in FIG. 7 in parallel with the horizontal direction are also described below.

FIG. 8 shows an example of the measurement results of the emission intensity of an emission line derived from lead (405.78 nm) when a decinormal nitric acid solution containing 100 ppm lead was supplied as a sample solution to the flow channel and a voltage was applied to generate plasma emission with the method described in Embodiment 1. The coefficient of variation of the emission intensity for each arrangement direction of the flow channel is described using as variables the flow rate of the sample and the time during which no voltage is applied between voltage application pulses.

When the flow channel is arranged in the horizontal direction for comparison purposes, it is seen that a sufficiently small coefficient of variation is obtained under the left most conditions in which each of the flow rate and the inter-pulse duration is large, and thus the reproducibility of the measured emission intensity is high, whereas in the middle conditions in which the flow rate is reduced and under the right most conditions in which the inter-pulse duration is shortened, the coefficient of variation has increased to about 10%, which show that the reproducibility is decreased.

In contrast, when the flow channel is arranged in parallel with the vertical direction, it is seen that a small coefficient of variation is obtained under the leftmost conditions in which each of the flow rate and the inter-pulse duration is large, and thus, the reproducibility of the measured emission intensity is high, whereas even under the middle conditions in which the flow rate is reduced and under the rightmost conditions in which the inter-pulse duration is shortened, the coefficient of variation remains within 5%, which shows that the reproducibility is maintained relatively high in comparison with a case where the flow channel is arranged in the horizontal direction. That is, according to this method, the volume of the sample used can be reduced by about 30% or about 12% than that of the conventional spectrometer. Thus, measurement of a small amount of sample solution becomes easy.

When the flow channel is arranged in parallel with the vertical line, the generated air bubbles can easily move toward the outlet side of the flow channel more due to the buoyancy of the air bubbles. This is one of the reasons for the above effect. In order to increase the buoyancy effect, it is most desirable that a line that connects the center of the flow channel be a straight line and the straight line be parallel with the vertical line. Even if the flow channel is arranged in not perfectly parallel with the vertical line, sufficient buoyancy will act as long as the internal angle between a line that connects the center of the flow channel and the vertical line is less than or equal to 60°, which is effective. Meanwhile, arranging the narrow portion in parallel with the vertical line is also effective. In such a case, even if the narrow portion is arranged not in perfectly parallel with the vertical line, a sufficient advantageous effects will be obtained if the internal angle between a the narrow portion and the vertical line is less than or equal to 60°. In any case, the movement direction of a fluid is preferably set in a direction from the lower end to the upper end of the vertical direction.

Although this embodiment has described an example of a specific flow channel configuration, the scope of the present invention is not limited thereto, and is also effective for other flow channels shapes.

[Embodiment 3]

This embodiment will describe another example of a flow channel shape in a plasma spectrometer. In the illustrated drawings, a narrow portion, connection portions, and main portions of the flow channel are displayed together with the shape of the flow channel.

FIG. 9A is a diagram illustrating an example of a flow channel of a plasma spectrometer. In this example, the cross-section of a narrow portion is circular unlike in the flow channel 100 shown in FIG. 1A. In addition, the configurations of the cylindrical connection portions of the flow channel that are arranged on the opposite sides (right and left sides) of the narrow portion are adjusted to have different diameters and lengths. Even when such a shape is adopted, the symmetry of expansion of each connection portion of the flow channel is maintained, and the conditions that each main portion of the flow channel should have no change in the cross-sectional shape, and the flow channel should be straight are ensured.

One of the characteristic effects of the flow channel shown in FIG. 9A is that it is possible to perform design of the adequate size in accordance with air bubbles that spread toward the right and left sides of the narrow portion. As can be seen from the view of air bubbles generated upon application of a voltage shown in FIG. 6A, the way in which the air bubbles spread toward the opposite sides of the narrow portion is not uniform. Thus, by selecting a flow channel diameter in accordance with the size of air bubbles on each side of the narrow portion, it becomes possible to avoid a problem that the interface of the air bubbles may reach the electrode arranged at the end of the flow channel, which could cause flow of an overcurrent and thus could damage the flow channel. In addition, by adjusting the diameter of the flow channel, it is also possible to provide a condition in which the applied voltage is concentrated not on a solution but on the air bubble portions, which allows analysis with high reproducibility.

FIG. 9B is a diagram illustrating another example of a flow channel of a plasma spectrometer. In this example, main portions of the flow channel on the opposite sides of a narrow portion are formed to be not cylindrical in shape but substantially conical in shape, unlike in the flow channel 100 shown in FIG. 1A. "Substantially conical in shape" includes a shape that has a certain high degree of axial symmetry and in which the cross-sectional area simply changes along the axis, like a conical shape, an elliptical conical shape, a polygonal conical shape, or the like. When such a shape is adopted, the symmetry of expansion of each connection portion of the flow channel is maintained, and the conditions that the flow channel should be straight are ensured.

One of the characteristic effects of the flow channel shown in FIG. 9B is that even when the volume of air bubbles that spread toward the right and left sides of the narrow portion has changed more or less, the distance between the gas-liquid interfaces generated on the opposite sides of the narrow portion is unlikely to be influenced, and thus, the reproducibility of the emission intensity for each voltage application pulse improves. The longer the distance from the narrow portion, the larger the cross-sectional area of the flow channel. Thus, even when the volume of air bubbles has increased, the distance between the gas-liquid interfaces will be influenced only to a degree that is smaller than the amount that is proportional to the volume. The electrostatic discharge phenomenon in air bubbles is greatly influenced by the intensity of an electric field applied to the air bubbles, and such influence depends on the distance between the gas-liquid interfaces. Thus, the fact that the distance between the gas-liquid interfaces does not greatly change has the effect of improving the reproducibility of the emission intensity, and thus, analysis with high reproducibility becomes possible.

Likewise, there is another advantageous effect that range of the applicable voltage conditions can be increased. Typically, when the conditions of the applied voltage are changed, the size of air bubbles will change. Thus, the optimal length of the flow channel will differ depending on the conditions of the applied voltage. However, in the flow channel herein, the influence of a change in the size of air bubbles on the distance between the gas-liquid interfaces is relatively small. Thus, there will be only small influence even when the voltage application conditions are changed.

Figure 9C:
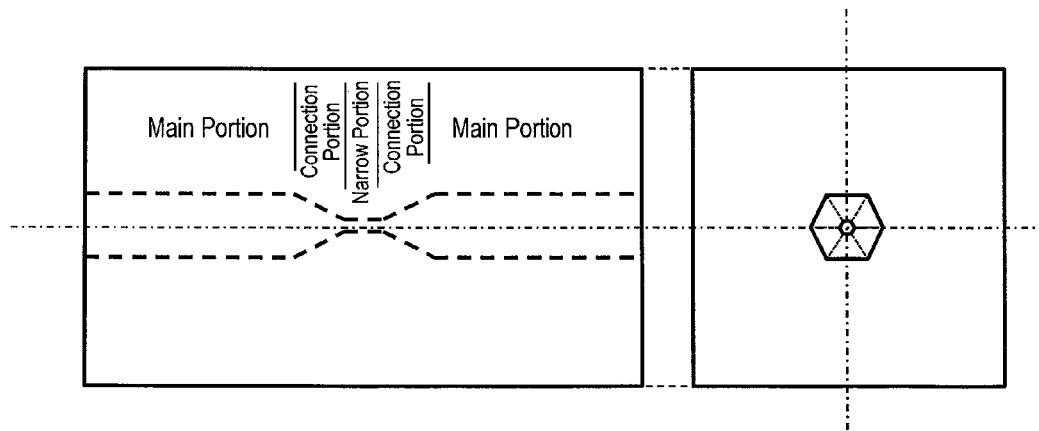
FIG. 9C is a diagram showing an exemplary flow channel.

FIG. 9C is a diagram showing another exemplary flow channel of a plasma spectrometer. In this example, the flow channel cross-sections of a narrow portion, connection portions of the flow channel, and main portions of the flow channel are regular hexagons unlike in the flow channel 100 in FIG. 1A. Even when such a shape is adopted, the symmetry of expansion of each connection portion of the flow channel is maintained, and the conditions that each main portion of the flow channel should have no change in the cross-sectional shape and the flow channel should be straight are ensured.

One of the characteristic effects of the flow channel shown in FIG. 9C is that another creation method can be used for creating the flow channel. The most common method for creating a flow channel with a cylindrical shape such as the flow channel 100 is processing with the use of a drill. One of the advantageous effects of selecting the shape of the flow channel 100 is that the processing cost of the flow channel can be reduced as the drill machining can be adopted, and thus that the cost of an analysis device can be reduced. However, there are problems that the narrow portion of the flow channel may become clogged with cutting scraps that are produced during a cutting process, which in turn makes it difficult to clean the flow channel, and it is difficult to polish the inner surface of the flow channel sufficiently smoothly. When the flow channel cross-section is formed in a polygonal shape, it becomes easier to form a flow channel with a shape in which the flow channel is divided into two on a plane that includes the center axis of the flow channel through a cutting process. In such a case, bonding the two portions of the flow channel together later to complete the flow channel can avoid the above problem. Although the flow channel cross-section of a regular hexagon is shown in this embodiment, it is also effective to adopt flow channel cross-sections of other polygonal shapes, such as a quadrangle or an octagon.

Figure 9D:
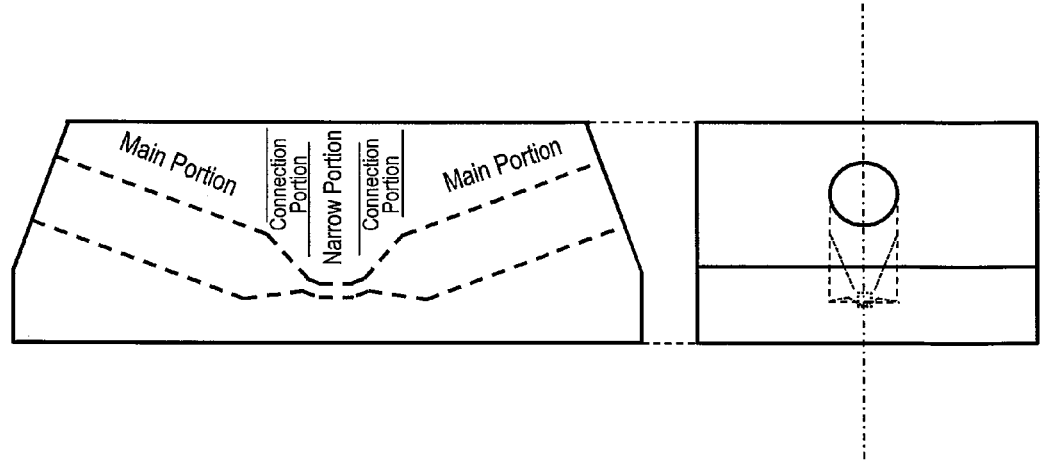
FIG. 9D is a diagram showing an exemplary flow channel.

FIG. 9D is a diagram showing another exemplary flow channel of a plasma spectrometer. In this example, main portions of the flow channel are connected to a narrow portion at a slightly inclined angle unlike in the flow channel 100 shown in FIG. 1A. When end portions of the narrow portion are also tilted like the connection portions and the main portions of the flow channel, it is also possible with this shape to maintain the symmetry of expansion of each connection portion of the flow channel. In addition, the conditions that each main portion of the flow channel should have no change in the cross-sectional shape and a curve of the flow channel should be sufficiently small are ensured.

One of the characteristic effects of the flow channel shown in FIG. 9D is that the narrow portion can be easily arranged close to the wall of the material that forms the flow channel. The shape of the flow channel herein is different from those shown in FIGS. 1A, 9A, 9B, and 9C. Thus, it is possible to reduce the thickness of the material of the flow channel on the lower side of the drawing seen from each narrow portion. Plasma emission is considered to spread equally in all directions from the emission place, and the amount of light that can be received is considered to be inversely proportional to the square of the distance from the emission place. Thus, when the narrow portion is arranged closer to the wall, it becomes possible to bring a light receiving portion closer to the light emission portion and thus improve the detection sensitivity. When an example is considered in which light is received by arranging an optical fiber end at a position close to the wall of the material that forms the flow channel, the flow channel 100 shown in FIG. 1A needs a distance of about 2.5 mm, and the flow channel shown in FIG. 9D needs a distance of about 0.5 mm. Thus, the amount of light that is received with the flow channel in FIG. 9D is 25 times that of the flow channel in FIG. 1A. Thus, there is a significant advantageous effect in that the detection sensitivity can be increased.

Figure 9E:
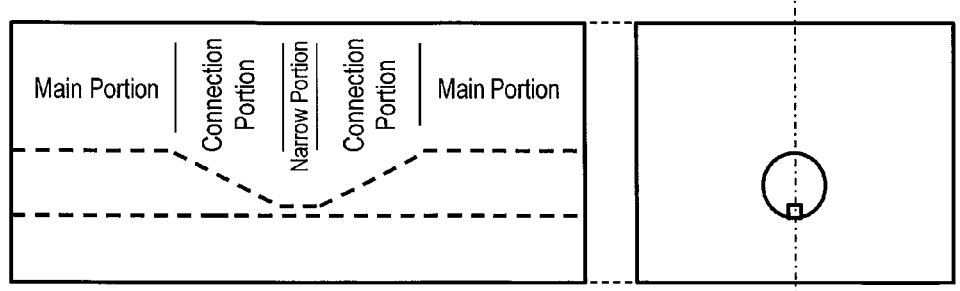
FIG. 9E is a diagram showing an exemplary flow channel.

FIG. 9E is a diagram illustrating another exemplary flow channel of a plasma spectrometer. In the example herein, the center axis of a narrow portion deviates from the center axes of main portions of the flow channel unlike in the flow channel 100 shown in FIG. 1A. The ratio of the amount of deviation to the width of the flow channel cross-section of each main portion in the direction of deviation is less than or equal to ½. The conditions that each main portion of the flow channel should have no change in the cross-sectional shape and that the flow channel should be straight are ensured.

One of the characteristic effects of the flow channel shown in FIG. 9E is that the narrow portion can be easily arranged close to the wall of the material that forms the flow channel as in the flow channel shown in FIG. 9D. When the flow channel herein is compared with those shown in FIGS. 1A, 9A, 9B and 9C, the way in which the flow channel expands is different. Thus, it is possible to reduce the thickness of the material that forms the flow channel on the lower side of the drawing seen from each narrow portion. Consequently, detection sensitivity can be improved as in FIG. 9D. Further, when the flow channel herein is compared with the flow channel shown in FIG. 9D, there are advantageous effects in that the flow channel structure is simple and the processing cost of the flow channel is reduced. When the flow channel herein is compared with that shown in FIG. 3A, there are advantageous effects in that as the flow channel is not curved, air bubbles that are generated upon application of a voltage can be easily removed with the flow of a sample solution during the time between voltage pulses, and thus, the reproducibility of the emission intensity can be improved.

Although this embodiment has illustrated exemplary shapes of flow channels in a plasma spectrometer, the present invention is limited thereto. In addition, although the arrangement direction of the flow channel has not been described, the flow channel may also be effectively arranged in the vertical direction and used.

[Embodiment 4]

This embodiment will describe an example of a plasma spectrometer in which measurement is performed in a region other than a narrow portion.

Figure 10A:
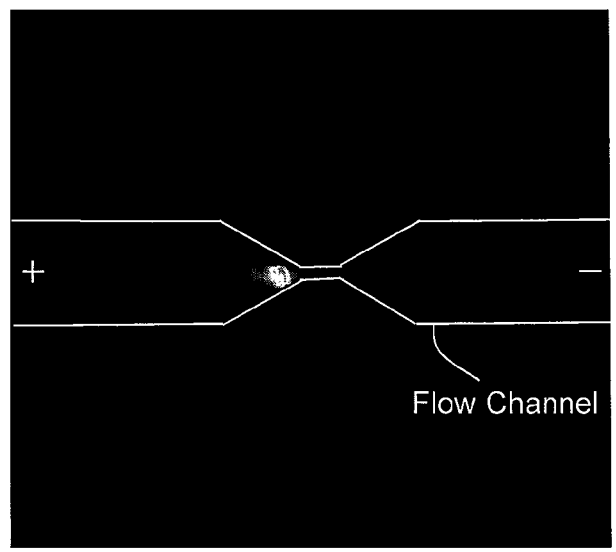
FIG. 10A is a diagram showing an exemplary distribution of the atomic emission in a flow channel.

FIG. 10A is a diagram showing an exemplary distribution of the atomic emission in the flow channel 100 shown in FIG. 1A. A decinormal nitric acid solution containing 100 ppm lead was used as a sample solution, and a voltage of 1.6 kV was applied for 20 milliseconds. A voltage was applied with the left side of the drawing being a positive electrode and the right side being a negative electrode. A distribution of the light emission was measured through a bandpass filter with a center wavelength of 405 nm and a half width of 10 nm that passes atomic emission of lead (405.78 nm). Light that was obtained by performing measurement under similar conditions by using a decinormal nitric acid solution not containing lead as a sample solution was regarded as the background light, and a distribution of the background light was subtracted from the previously obtained light emission distribution to obtain only a distribution of the atomic emission of lead. When the distribution of the atomic emission of lead is seen, strong light emission is found in the connection portion of the flow channel on the positive electrode side that is adjacent to the narrow portion. Therefore, it is found that performing measurement in a connection portion, in particular, the connection portion on the positive electrode side can provide higher sensitivity than and thus is more advantageous than performing measurement in the narrow portion as has been conventionally done.

Figure 10B:
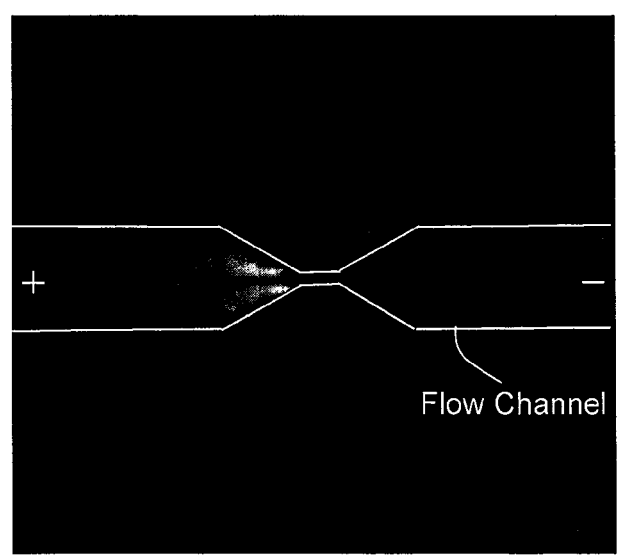
FIG. 10B is a diagram showing an exemplary distribution of the intensity ratio of the atomic emission to the background light in a flow channel.

FIG. 10B is a diagram showing an exemplary distribution of the intensity ratio of the atomic emission to the background light in the flow channel 100. This drawing shows the intensity ratio of the atomic emission of lead to the background light that have been obtained with the method described in the previous paragraph. In the drawing, white color is displayed stronger as the ratio of the intensity of the atomic emission to the intensity of the background light is higher. When the distribution of the intensity ratio is seen, a higher ratio is found in the connection portion of the flow channel on the positive electrode side that is adjacent to the narrow portion than in the narrow portion. A higher intensity ratio of the atomic emission to the background light is more advantageous in performing high-sensitivity measurement. Thus, it is found that performing measurement in a region that is adjacent to the narrow portion, in particular, the connection portion on the positive electrode side can provide higher sensitivity and thus is more advantageous than performing measurement in the narrow portion as has been conventionally done. Further, when the distribution is overlaid on the images captured with a high-speed camera shown in FIGS. 6A and 6B, it is found that the distribution is the same as the distribution of the gas-liquid interface around the connection portion on the positive electrode side. Therefore, it is found that performing measurement in an area adjacent to the narrow portion, in particular, around the gas-liquid interface in the connection portion on the positive electrode side is advantageous in performing high-sensitivity measurement. As the gas-liquid interface is located at a position closer to the wall of the flow channel than to a portion that extends from the narrow portion of the flow channel, it is found that performing measurement in the connection portion on the positive electrode side, in particular, in an area close to the wall of the flow channel excluding the center of the flow channel is advantageous in performing high-sensitivity measurement.

The fact that the effect described herein is dependent on the voltage application direction has been confirmed by conducting an experiment of reversing the voltage application direction and seeing the result that a region with high emission intensity appeared on the right side of the narrow portion. One of the reasons why a prominent effect can be seen on the positive electrode side, in particular, is that a characteristic gas-liquid interface such as the one shown in FIG. 6A is formed. One of the reasons why such a characteristic gas-liquid interface is formed is considered to be that the direction of an electroosmotic flow that is generated along the inner wall of the flow channel upon application of a voltage is the direction from the positive electrode side to the negative electrode side, and thus a solution is pushed from the positive electrode side to the narrow portion along the wall.

Figure 11A:
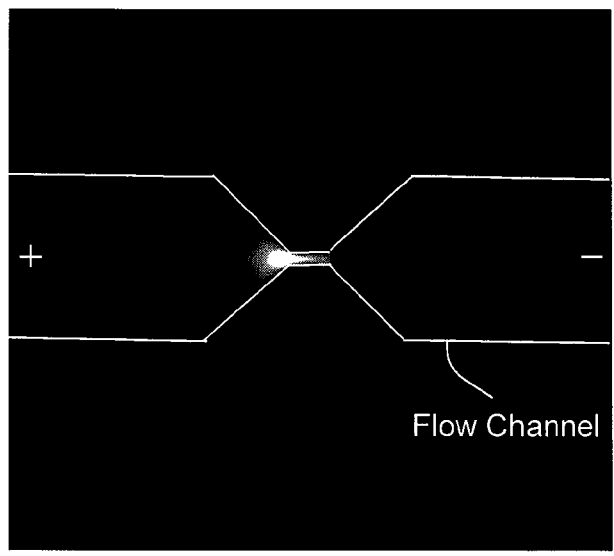
FIG. 11A is a diagram showing an exemplary distribution of the atomic emission in a flow channel.
Figure 11B:
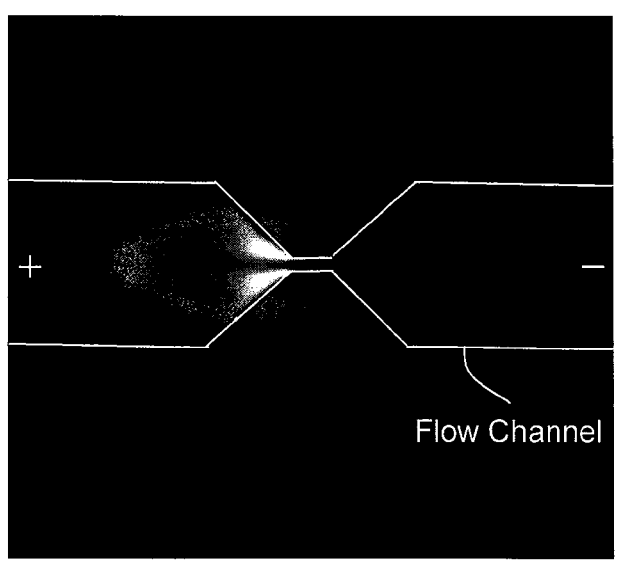
FIG. 11B is a diagram showing an exemplary distribution of the intensity ratio of the atomic emission to the background light in a flow channel.

The effect exemplarily shown in FIGS. 10A and 10B can be found not only in the flow channel 100 shown in FIG. 1A. FIG. 11A shows a distribution of, when the same measurement was performed on the flow channel 200 shown in FIG. 3A, atomic emission obtained from the bottom face side of the flow channel, and FIG. 11B shows a distribution of the intensity ratio of the obtained atomic emission to the background light. When the distribution of the atomic emission of lead in FIG. 11A is seen, light emission can be confirmed even in the narrow portion, but strong light emission is found in the connection portion of the flow channel on the positive electrode side. Further, when the intensity ratio of the atomic emission of lead to the background light in FIG. 11B is seen, it is found that a similar distribution to that in FIG. 10B is obtained.

Figure 12A:
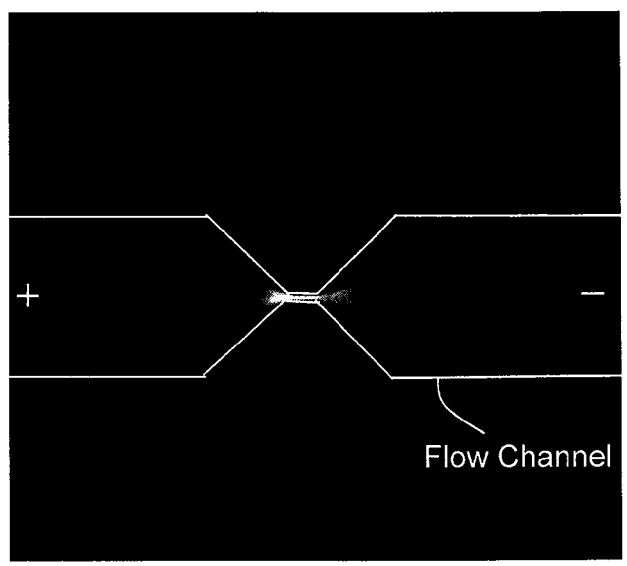
FIG. 12A is a diagram showing an exemplary distribution of the atomic emission in a flow channel.
Figure 12B:
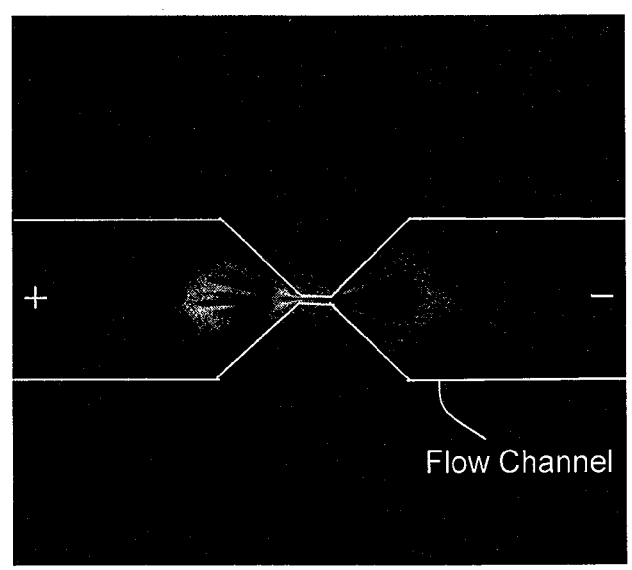
FIG. 12B is a diagram showing an exemplary distribution of the intensity ratio of the atomic emission to the background light in a flow channel.

It has also been found that a similar effect can be obtained even with a planar flow channel. FIG. 12A shows a distribution of, when the same measurement was performed on the flow channel 300 shown in FIG. 4A that has a connection angle of the connection portion of 45°, atomic emission obtained from the bottom face side of the flow channel, and FIG. 12B shows a distribution of the intensity ratio of the obtained atomic emission to the background light. Herein, a voltage of 2.5 kV was applied for 1.8 milliseconds. When the distribution of the atomic emission of lead in FIG. 12A is seen, light emission can be confirmed even in the narrow portion, but atomic emission with a similar intensity level is also found in the connection portion of the flow channel on the positive electrode side. Further, when the intensity ratio of the atomic emission of lead to the background light in FIG. 12B is seen, it is found that a region where the intensity ratio of the atomic emission to the background light is high is located in the connection portion on the positive electrode side. Accordingly, when measurement is performed in the connection portion on the positive electrode side that is adjacent to the narrow portion as with the flow channels 100 and 200, it becomes possible to perform high-sensitivity measurement than performing measurement in the narrow portion as has been conventionally done.

[Embodiment 5]

This embodiment will describe an example of a plasma spectrometer in which a narrow portion of a flow channel is arranged in parallel with the vertical line.

Figures 13, 14:
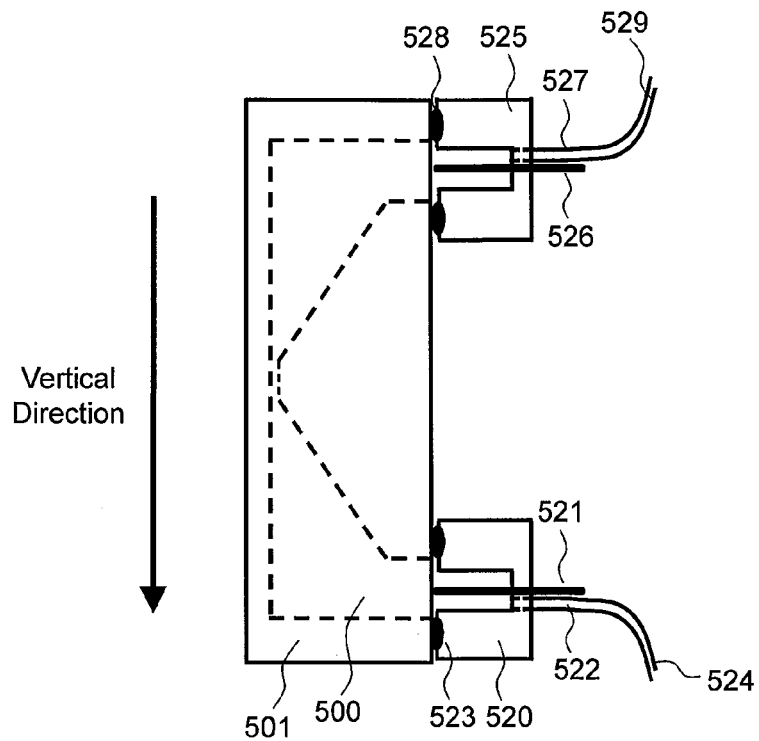
FIG. 13 is a diagram showing an exemplary plasma spectrometer in which a narrow portion of a flow channel is arranged in parallel with the vertical line.
FIG. 14 is a diagram showing coefficients of variation of the emission intensity of lead.

FIG. 13 is a diagram illustrating an exemplary arrangement of a flow channel 500 of a plasma spectrometer in this embodiment. The flow channel 500 is a flow channel with a similar shape to the flow channel 200. The flow channel 500 is created in quartz glass 501. The flow channel 500 is arranged such that the orientation of the narrow portion thereof is parallel with the vertical direction. As in FIG. 3B, at the lower side end of the flow channel 500, a connector 520 is connected to the quartz glass 501 via an O-ring 523 using a pressure method to avoid leakage of liquid that would occur when the liquid is flowed from the outside. An electrode 521 and a pipe connection port 522 are fixed to the connector 520. A pipe 524 is connected to the pipe connection port 522. A tip end of the electrode 521 is arranged such that it is located at an end of the flow channel 500. As with the lower side end of the flow channel 500, an O-ring 528, a connector 525, an electrode 526, a pipe connection port 527, and a pipe 529 are arranged at the upper side end.

When plasma spectroscopy was performed, portions shown in FIG. 1B of the schematic diagram of the exemplary configuration of the plasma spectrometer shown in FIG. 2 were replaced with portions shown in FIG. 13, and the position of the optical fiber end 143 was adjusted to the position of the flow channel 500. The pipe 524 and the pipe 529 were connected to the syringe pump 140 and the waste liquid container 141, respectively, so that the liquid transfer direction of the sample solution became the direction from the lower side of the vertical direction to the upper side of the vertical direction.

In this embodiment, comparison was made between a case where the electrode 526 on the upper side of the vertical direction was used as a positive electrode and a case where it was used as a negative electrode in order to study a case where the flow channel is arranged in the vertical line, inclusive of the polarity of the electrode. The results are described below together with the measurement results of light emission obtained by arranging the flow channel in FIG. 13 in parallel with the horizontal direction.

FIG. 14 shows an example of the measurement results of the emission intensity of an emission line derived from lead (405.78 nm) when a decinormal nitric acid solution containing 100 ppm lead was supplied as a sample solution to the flow channel and a voltage of 800 V was applied for 2 milliseconds to generate plasma emission with the method described in Embodiment 1. The coefficients of variation of the emission intensity are described using as variables the arrangement of the flow channel and, when the flow channel is arranged in the vertical direction, the polarity of the upper electrode.

When the flow channel is arranged in the horizontal direction, the coefficient of variation of the emission intensity is high, and thus, the result of low reproducibility is obtained. This is partly because of the low axial symmetry of the flow channel. Meanwhile, when the flow channel is located in parallel with the vertical direction, the coefficient of variation of the emission intensity is lower than when the flow channel is arranged in the horizontal direction regardless of the arrangement of the electrode, and thus, the result of high reproducibility is obtained. That is, when the flow channel is arranged in parallel with the vertical direction, the reproducibility can be improved.

Further, when the electrode 526 on the upper side of the vertical direction is used as a negative electrode, the coefficient of variation can be smaller and the result of higher reproducibility is thus obtained in comparison with a case where the electrode 526 is used as a positive electrode. A variety of possible influence of the electrode polarity on the reproducibility is considered, and one of them is that air bubbles are generated more on the negative electrode side than on the positive electrode side. Avoiding stagnation of air bubbles that are generated upon application of a voltage can improve the reproducibility. Thus, it is considered that the reproducibility is higher when the electrode on the upper side of the vertical direction is used as a negative electrode as air bubbles generated on the negative electrode side will not enter the flow channel.

Although this embodiment has described an exemplary configuration of a specific flow channel, the scope of the present invention is not limited thereto, and is also effective for other flow channel shapes.

It should be noted that the present invention is not limited to the aforementioned embodiments, and includes a variety of variations. For example, although the aforementioned embodiments have been described in detail to clearly illustrate the present invention, the present invention need not include all of the structures described in the embodiments. It is possible to replace a part of a structure of an embodiment with a structure of another embodiment. In addition, it is also possible to add, to a structure of an embodiment, a structure of another embodiment. Further, it is also possible to, for a part of a structure of each embodiment, add/remove/substitute a structure of another embodiment.

In addition, although the aforementioned embodiments have been described using the limited elements, solution composition, and measurement conditions as examples, the present invention is not limited thereto.

REFERENCE SIGNS LIST 100, 200, 300, 400: Flow channel
101, 201, 301, 401: Quartz glass
120, 125, 220, 225, 320, 325, 420, 425, 520, 525: Connector
121, 126, 221, 226, 321, 326, 421, 426, 521, 526: Electrode
122, 127, 222, 227, 322, 327, 422, 427, 522, 527: Pipe connection port
123, 128, 223, 228, 323, 328, 423, 428, 523, 528: O-ring
124, 129, 224, 229, 324, 329, 424, 429, 524, 529: Pipe
140: Syringe pump
141: Waste liquid container
143: Optical fiber end
144: Optical fiber
145: Spectroscope
146: Imaging device
150: Computer
147, 148, 149, 151, 153: Signal line
152: Power supply
154: Ammeter
155, 156: High-voltage cable

The invention claimed is:

1. A plasma spectrometer comprising:
a flow channel supplied with a sample solution, the flow channel including a narrow portion, main portions each having a larger flow channel cross-section than a flow channel cross-section of the narrow portion, and connection portions each connecting the narrow portion and one of the main portions;
a pair of electrodes arranged so as to interpose the main portions therebetween, the pair of electrodes being configured to apply a voltage to the flow channel; and
a detector to measure plasma emission generated in air bubbles that are generated in the sample solution in the flow channel upon application of the voltage,
wherein each of the connection portions is substantially conical in shape, and each of the main portions is substantially cylindrical in shape, and
wherein the electrodes are arranged to extend along a central axis of the narrow portion.

2. The plasma spectrometer according to claim 1, wherein in a flow channel cross-section that is perpendicular to a center axis of each connection portion of the flow channel, a length ratio of a longest line segment that passes through a center to a shortest line segment that passes through the center is less than or equal to 2:1.

3. The plasma spectrometer according to claim 1, wherein in a flow channel cross-section of each main portion, a length ratio of a longest line segment that passes through a center to a shortest line segment that passes through the center is less than or equal to 2:1.

4. The plasma spectrometer according to claim 1, wherein a change rate of a flow channel cross-sectional area that is perpendicular to a line that connects a center of each main portion is less than or equal to 2.

5. The plasma spectrometer according to claim 1, wherein a curve of a line that connects a center of each main portion is less than or equal to 60°.

6. The plasma spectrometer according to claim 1, wherein a ratio of an amount of positional deviation between a center axis of the narrow portion and a center axis of each main portion to a width of a flow channel cross-section of the main portion in a direction of the deviation is less than or equal to ½.

7. The plasma spectrometer according to claim 1, wherein a width of each main portion in a vertical direction is equal to or less than a width of the main portion in a horizontal direction.

8. The plasma spectrometer according to claim 1, wherein the voltage applied by the electrodes is greater than or equal to 500V.

9. The plasma spectrometer according to claim 1, wherein the voltage is applied by the electrodes for at least 0.1 ms.

10. The plasma spectrometer according to claim 1, wherein a width of the narrow portion is less than ⅓ a width of the main portions.

11. The plasma spectrometer according to claim 1, wherein a length of the narrow portion is less than ⅕ an overall length of the flow channel, and
wherein the overall length of the flow channel is greater than or equal to 1 mm and less than or equal to 300 mm.

12. The plasma spectrometer according to claim 1, further comprising:
a pair of connectors which are connected to the flow cell and hold the electrodes to so as to interpose the main portions therebetween, and
wherein the electrodes are respectively arranged at the ends of the main portions.

13. The plasma spectrometer according to claim 1, wherein the narrow portion has a square cross-section.

* * * * *